US012611520B2

(12) United States Patent (10) Patent No.: US 12,611,520 B2

Howell (45) Date of Patent: Apr. 28, 2026

(54) RAPIDLY INSERTABLE CENTRAL CATHETER AND METHODS THEREOF

(71) Applicant: Bard Access Systems, Inc., Salt Lake City, UT (US)

(72) Inventor: Glade H. Howell, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 789 days.

(21) Appl. No.: 17/077,728

(22) Filed: Oct. 22, 2020

(65) Prior Publication Data

US 2021/0113810 A1 Apr. 22, 2021

Related U.S. Application Data

(60) Provisional application No. 62/924,582, filed on Oct. 22, 2019.

(51) Int. Cl.
*A61M 25/00* (2006.01)
*A61M 25/06* (2006.01)

(52) U.S. Cl.
CPC .... *A61M 25/0026* (2013.01); *A61M 25/0097* (2013.01); *A61M 25/0606* (2013.01); *A61M 25/0637* (2013.01); *A61M 2205/0205* (2013.01)

(58) Field of Classification Search
CPC .......... A61M 25/0054; A61M 25/0026; A61M 25/0097; A61M 25/0606; A61M 25/0637;
(Continued)

(56) References Cited

U.S. PATENT DOCUMENTS 1,013,691 A 1/1912 Shields
3,225,762 A 12/1965 Guttman
(Continued)

FOREIGN PATENT DOCUMENTS

DE 102018102390 A1 8/2019
EP 0730880 A1 9/1996
(Continued)

OTHER PUBLICATIONS

PCT/US2020/048583 filed Aug. 28, 2020 International Search Report and Written Opinion dated Nov. 13, 2020.
(Continued)

*Primary Examiner* — Chelsea E Stinson
*Assistant Examiner* — Robert F Allen
(74) *Attorney, Agent, or Firm* — Rutan & Tucker LLP

(57) ABSTRACT

Rapidly insertable central catheters ("RICC") and methods thereof are disclosed. In an example, a RICC includes a catheter tube, a suture wing disposed over a medial portion of the catheter tube, a hub coupled to a proximal-end portion of the catheter tube, and a number of extension legs extending from the hub. The catheter tube can include a first section in a distal portion of the catheter tube formed of a first polymeric material having a first durometer. The catheter tube can also include a second section proximal of the first section of the catheter tube formed of a second polymeric material having a second durometer less than the first durometer. The catheter tube can have a column strength sufficient to prevent buckling of the catheter tube when inserted into an insertion site and advanced through a vasculature of a patient without use of the Seldinger technique.

16 Claims, 5 Drawing Sheets

(58) Field of Classification Search
CPC ...... A61M 2205/0205; A61M 25/0014; A61M
25/0021; A61M 25/007; A61M
2025/0059; A61M 25/0053; A61M
2025/0286; A61M 225/0026; A61M
25/0029
See application file for complete search history.

(56) References Cited

U.S. PATENT DOCUMENTS

| | | | |
|---|---|---|---|
| 3,890,976 A * | 6/1975 | Bazell | A61M 25/008 |
| | | | 128/207.15 |
| 4,205,675 A | 6/1980 | Vaillancourt | |
| 4,292,970 A | 10/1981 | Hession, Jr. | |
| 4,468,224 A | 8/1984 | Enzmann et al. | |
| 4,525,157 A | 6/1985 | Vaillancourt | |
| 4,581,019 A | 4/1986 | Curelaru et al. | |
| 5,017,259 A | 5/1991 | Kohsai | |
| 5,040,548 A | 8/1991 | Yock | |
| 5,057,073 A * | 10/1991 | Martin | A61M 5/1582 |
| | | | 604/523 |
| 5,112,312 A | 5/1992 | Luther | |
| 5,120,317 A | 6/1992 | Luther | |
| 5,129,891 A | 7/1992 | Young | |
| 5,135,599 A * | 8/1992 | Martin | A61M 25/0028 |
| | | | 604/523 |
| 5,149,330 A | 9/1992 | Brightbill | |
| 5,167,623 A | 12/1992 | Cianci et al. | |
| 5,188,593 A * | 2/1993 | Martin | B29C 65/18 |
| | | | 604/6.05 |
| 5,195,962 A * | 3/1993 | Martin | A61M 25/003 |
| | | | 604/43 |
| 5,207,650 A * | 5/1993 | Martin | A61M 25/0026 |
| | | | 604/173 |
| 5,267,958 A | 12/1993 | Buchbinder et al. | |
| 5,295,970 A | 3/1994 | Clinton et al. | |
| 5,306,247 A | 4/1994 | Pfenninger | |
| 5,328,472 A | 7/1994 | Steinke et al. | |
| 5,350,358 A * | 9/1994 | Martin | A61M 25/0041 |
| | | | 604/507 |
| 5,364,377 A | 11/1994 | O'Neil | |
| 5,368,567 A | 11/1994 | Lee | |
| 5,378,230 A | 1/1995 | Mahurkar | |
| 5,380,290 A | 1/1995 | Makower et al. | |
| 5,389,087 A | 2/1995 | Miraki | |
| 5,405,341 A * | 4/1995 | Martin | A61M 1/3661 |
| | | | 604/523 |
| 5,439,449 A | 8/1995 | Mapes et al. | |
| 5,443,457 A | 8/1995 | Ginn et al. | |
| 5,489,271 A | 2/1996 | Andersen | |
| 5,573,520 A | 11/1996 | Schwartz et al. | |
| 5,683,370 A * | 11/1997 | Luther | A61M 25/001 |
| | | | 604/528 |
| 5,718,678 A | 2/1998 | Fleming, III | |
| 5,772,636 A | 6/1998 | Brimhall et al. | |
| 5,885,251 A | 3/1999 | Luther | |
| 5,919,164 A | 7/1999 | Andersen | |
| 5,947,940 A | 9/1999 | Beisel | |
| 5,957,893 A | 9/1999 | Luther et al. | |
| 6,066,489 A | 5/2000 | Fields et al. | |
| 6,074,379 A * | 6/2000 | Prichard | A61M 25/0097 |
| | | | 604/524 |
| 6,206,849 B1 | 3/2001 | Martin et al. | |
| 6,377,856 B1 | 4/2002 | Carson | |
| 6,475,187 B1 | 11/2002 | Gerberding | |
| 6,606,515 B1 | 8/2003 | Windheuser et al. | |
| 6,716,228 B2 | 4/2004 | Tal | |
| 6,726,659 B1 | 4/2004 | Stocking et al. | |
| 6,819,951 B2 | 11/2004 | Patel et al. | |
| 6,821,287 B1 | 11/2004 | Jang | |
| 6,926,692 B2 | 8/2005 | Katoh et al. | |
| 6,962,575 B2 | 11/2005 | Tal | |
| 6,994,693 B2 | 2/2006 | Tal | |
| 6,999,809 B2 | 2/2006 | Currier et al. | |
| 7,025,746 B2 | 4/2006 | Tal | |

| | | | | |
|---|---|---|---|---|
| 7,029,467 B2 | 4/2006 | Currier et al. | | |
| 7,037,293 B2 | 5/2006 | Carrillo et al. | | |
| 7,074,231 B2 | 7/2006 | Jang | | |
| 7,141,050 B2 | 11/2006 | Deal et al. | | |
| 7,144,386 B2 | 12/2006 | Korkor et al. | | |
| 7,311,697 B2 | 12/2007 | Osborne | | |
| 7,364,566 B2 | 4/2008 | Elkins et al. | | |
| 7,377,910 B2 | 5/2008 | Katoh et al. | | |
| 7,390,323 B2 | 6/2008 | Jang | | |
| D600,793 S | 9/2009 | Bierman et al. | | |
| D601,242 S | 9/2009 | Bierman et al. | | |
| D601,243 S | 9/2009 | Bierman et al. | | |
| 7,594,911 B2 | 9/2009 | Powers et al. | | |
| 7,691,093 B2 | 4/2010 | Brimhall | | |
| 7,722,567 B2 | 5/2010 | Tal | | |
| D617,893 S | 6/2010 | Bierman et al. | | |
| D624,643 S | 9/2010 | Bierman et al. | | |
| 7,819,889 B2 | 10/2010 | Healy et al. | | |
| 7,857,788 B2 | 12/2010 | Racz | | |
| D630,729 S | 1/2011 | Bierman et al. | | |
| 7,909,797 B2 | 3/2011 | Kennedy, II et al. | | |
| 7,909,811 B2 | 3/2011 | Agro et al. | | |
| 7,922,696 B2 | 4/2011 | Tal et al. | | |
| 7,938,820 B2 | 5/2011 | Webster et al. | | |
| 7,967,834 B2 | 6/2011 | Tal et al. | | |
| 7,985,204 B2 | 7/2011 | Katoh et al. | | |
| 8,073,517 B1 | 12/2011 | Burchman | | |
| 8,105,286 B2 | 1/2012 | Anderson et al. | | |
| 8,192,402 B2 | 6/2012 | Anderson et al. | | |
| 8,202,251 B2 | 6/2012 | Bierman et al. | | |
| 8,206,356 B2 | 6/2012 | Katoh et al. | | |
| 8,372,107 B2 | 2/2013 | Tupper | | |
| 8,377,006 B2 | 2/2013 | Tal et al. | | |
| 8,454,577 B2 | 6/2013 | Joergensen et al. | | |
| 8,585,858 B2 * | 11/2013 | Kronfeld | A61M 25/0054 | |
| | | | 156/203 | |
| 8,657,790 B2 | 2/2014 | Tal et al. | | |
| 8,672,888 B2 | 3/2014 | Tal | | |
| 8,696,645 B2 | 4/2014 | Tal et al. | | |
| 8,784,362 B2 | 7/2014 | Boutilette et al. | | |
| 8,827,958 B2 | 9/2014 | Bierman et al. | | |
| 8,876,704 B2 | 11/2014 | Golden et al. | | |
| 8,882,713 B1 | 11/2014 | Call et al. | | |
| 8,900,192 B2 | 12/2014 | Anderson et al. | | |
| 8,900,207 B2 | 12/2014 | Uretsky | | |
| 8,915,884 B2 | 12/2014 | Tal et al. | | |
| 8,956,327 B2 | 2/2015 | Bierman et al. | | |
| 9,023,093 B2 | 5/2015 | Pal | | |
| 9,138,252 B2 | 9/2015 | Bierman et al. | | |
| 9,180,275 B2 | 11/2015 | Helm | | |
| 9,265,920 B2 | 2/2016 | Rundquist et al. | | |
| 9,272,121 B2 | 3/2016 | Piccagli | | |
| 9,522,254 B2 | 12/2016 | Belson | | |
| 9,554,785 B2 | 1/2017 | Walters et al. | | |
| 9,566,087 B2 | 2/2017 | Bierman et al. | | |
| 9,675,784 B2 | 6/2017 | Belson | | |
| 9,713,695 B2 | 7/2017 | Bunch et al. | | |
| 9,764,117 B2 | 9/2017 | Bierman et al. | | |
| 9,770,573 B2 | 9/2017 | Golden et al. | | |
| 9,814,861 B2 | 11/2017 | Boutillette et al. | | |
| 9,820,845 B2 | 11/2017 | von Lehe et al. | | |
| 9,861,383 B2 | 1/2018 | Clark | | |
| 9,884,169 B2 | 2/2018 | Bierman et al. | | |
| 9,889,275 B2 | 2/2018 | Voss et al. | | |
| 9,913,585 B2 | 3/2018 | McCaffrey et al. | | |
| 9,913,962 B2 | 3/2018 | Tal et al. | | |
| 9,981,113 B2 | 5/2018 | Bierman | | |
| 10,010,312 B2 | 7/2018 | Tegels | | |
| 10,065,020 B2 | 9/2018 | Gaur | | |
| 10,098,724 B2 | 10/2018 | Adams et al. | | |
| 10,111,683 B2 | 10/2018 | Tsamir et al. | | |
| 10,118,020 B2 | 11/2018 | Avneri et al. | | |
| 10,130,269 B2 | 11/2018 | McCaffrey et al. | | |
| 10,220,184 B2 | 3/2019 | Clark | | |
| 10,220,191 B2 | 3/2019 | Belson et al. | | |
| 10,265,508 B2 | 4/2019 | Baid | | |
| 10,271,873 B2 | 4/2019 | Steingisser et al. | | |
| 10,376,675 B2 | 8/2019 | Mitchell et al. | | |
| 10,675,440 B2 | 6/2020 | Abitabilo et al. | | |

(56) References Cited

U.S. PATENT DOCUMENTS

| | | | |
|---|---|---|---|
| 10,806,901 B2 | 10/2020 | Burkholz et al. | |
| 2002/0040231 A1 | 4/2002 | Wysoki | |
| 2002/0198492 A1 | 12/2002 | Miller et al. | |
| 2003/0036712 A1 | 2/2003 | Heh et al. | |
| 2003/0060863 A1 | 3/2003 | Dobak | |
| 2003/0088212 A1 | 5/2003 | Tal | |
| 2003/0100849 A1 | 5/2003 | Jang | |
| 2003/0153874 A1 | 8/2003 | Tal | |
| 2003/0158514 A1 | 8/2003 | Tal | |
| 2004/0116901 A1 | 6/2004 | Appling | |
| 2004/0122418 A1 | 6/2004 | Voorhees | |
| 2004/0167478 A1 | 8/2004 | Mooney et al. | |
| 2004/0193093 A1* | 9/2004 | Desmond, III | A61M 27/008 |
| | | | 623/23.65 |
| 2004/0230178 A1 | 11/2004 | Wu | |
| 2005/0004554 A1 | 1/2005 | Osborne | |
| 2005/0245882 A1 | 11/2005 | Elkins et al. | |
| 2005/0261665 A1 | 11/2005 | Voorhees | |
| 2005/0283221 A1 | 12/2005 | Mann et al. | |
| 2006/0009740 A1 | 1/2006 | Higgins et al. | |
| 2006/0015086 A1 | 1/2006 | Rasmussen et al. | |
| 2006/0074380 A1 | 4/2006 | Mogensen et al. | |
| 2006/0116629 A1 | 6/2006 | Tal et al. | |
| 2006/0129100 A1 | 6/2006 | Tal | |
| 2006/0129130 A1 | 6/2006 | Tal et al. | |
| 2007/0078412 A1 | 4/2007 | McGuckin et al. | |
| 2008/0045894 A1* | 2/2008 | Perchik | A61M 25/0194 |
| | | | 604/96.01 |
| 2008/0125744 A1 | 5/2008 | Treacy | |
| 2008/0125748 A1 | 5/2008 | Patel | |
| 2008/0255447 A1* | 10/2008 | Bourang | A61M 31/005 |
| | | | 600/434 |
| 2008/0262430 A1 | 10/2008 | Anderson et al. | |
| 2008/0262431 A1 | 10/2008 | Anderson et al. | |
| 2008/0294111 A1 | 11/2008 | Tal et al. | |
| 2008/0306465 A1 | 12/2008 | Bailey et al. | |
| 2008/0312578 A1 | 12/2008 | DeFonzo et al. | |
| 2009/0221961 A1 | 9/2009 | Tal et al. | |
| 2009/0270889 A1 | 10/2009 | Tal et al. | |
| 2010/0125249 A1 | 5/2010 | Rosenberg et al. | |
| 2010/0256487 A1 | 10/2010 | Hawkins et al. | |
| 2010/0305474 A1 | 12/2010 | DeMars et al. | |
| 2011/0004162 A1 | 1/2011 | Tal | |
| 2011/0009827 A1 | 1/2011 | Bierman et al. | |
| 2011/0021994 A1 | 1/2011 | Anderson et al. | |
| 2011/0066142 A1 | 3/2011 | Tal et al. | |
| 2011/0144620 A1 | 6/2011 | Tal | |
| 2011/0152836 A1 | 6/2011 | Riopelle et al. | |
| 2011/0202006 A1 | 8/2011 | Bierman et al. | |
| 2011/0251559 A1 | 10/2011 | Tal et al. | |
| 2011/0270192 A1 | 11/2011 | Anderson et al. | |
| 2011/0319825 A1 | 12/2011 | Goral et al. | |
| 2012/0041371 A1 | 2/2012 | Tal et al. | |
| 2012/0065590 A1 | 3/2012 | Bierman et al. | |
| 2012/0078231 A1 | 3/2012 | Hoshinouchi | |
| 2012/0130411 A1 | 5/2012 | Tal et al. | |
| 2012/0130415 A1 | 5/2012 | Tal et al. | |
| 2012/0157854 A1 | 6/2012 | Kurrus et al. | |
| 2012/0220942 A1 | 8/2012 | Hall et al. | |
| 2012/0232498 A1 | 9/2012 | Ma et al. | |
| 2012/0239005 A1 | 9/2012 | Conway et al. | |
| 2012/0283640 A1 | 11/2012 | Anderson et al. | |
| 2012/0316500 A1 | 12/2012 | Bierman et al. | |
| 2013/0053826 A1 | 2/2013 | Shevgoor | |
| 2013/0123704 A1 | 5/2013 | Bierman et al. | |
| 2013/0150793 A1 | 6/2013 | Beissel et al. | |
| 2013/0158338 A1 | 6/2013 | Kelly et al. | |
| 2013/0188291 A1 | 7/2013 | Vardiman | |
| 2013/0218082 A1 | 8/2013 | Hyer et al. | |
| 2013/0237931 A1 | 9/2013 | Tal et al. | |
| 2013/0306079 A1 | 11/2013 | Tracy | |
| 2014/0025036 A1 | 1/2014 | Bierman et al. | |
| 2014/0081210 A1 | 3/2014 | Bierman et al. | |
| 2014/0100552 A1* | 4/2014 | Gallacher | A61M 39/20 |
| | | | 604/528 |
| 2014/0207052 A1 | 7/2014 | Tal et al. | |
| 2014/0207069 A1 | 7/2014 | Bierman et al. | |
| 2014/0214005 A1 | 7/2014 | Belson | |
| 2014/0257111 A1 | 9/2014 | Yamashita et al. | |
| 2014/0276432 A1 | 9/2014 | Bierman et al. | |
| 2014/0276599 A1 | 9/2014 | Cully et al. | |
| 2015/0051536 A1 | 2/2015 | Mendels et al. | |
| 2015/0080939 A1 | 3/2015 | Adams et al. | |
| 2015/0112310 A1 | 4/2015 | Call et al. | |
| 2015/0126930 A1 | 5/2015 | Bierman et al. | |
| 2015/0148595 A1 | 5/2015 | Bagwell et al. | |
| 2015/0190168 A1 | 7/2015 | Bierman et al. | |
| 2015/0196210 A1 | 7/2015 | McCaffrey et al. | |
| 2015/0224287 A1 | 8/2015 | Bian et al. | |
| 2015/0283357 A1 | 10/2015 | Lampropoulos et al. | |
| 2015/0297868 A1 | 10/2015 | Tal et al. | |
| 2015/0320969 A1 | 11/2015 | Haslinger et al. | |
| 2015/0351793 A1 | 12/2015 | Bierman et al. | |
| 2015/0359549 A1 | 12/2015 | Lenker et al. | |
| 2015/0359998 A1 | 12/2015 | Carmel et al. | |
| 2016/0067449 A1 | 3/2016 | Misener et al. | |
| 2016/0082223 A1 | 3/2016 | Barnell | |
| 2016/0114124 A1 | 4/2016 | Tal | |
| 2016/0220786 A1 | 8/2016 | Mitchell et al. | |
| 2016/0306393 A1 | 10/2016 | Huitema | |
| 2016/0325073 A1 | 11/2016 | Davies et al. | |
| 2016/0338728 A1 | 11/2016 | Tal | |
| 2016/0346503 A1* | 12/2016 | Jackson | A61M 25/0021 |
| 2017/0035990 A1 | 2/2017 | Swift | |
| 2017/0043126 A1 | 2/2017 | Jones et al. | |
| 2017/0072165 A1 | 3/2017 | Lim et al. | |
| 2017/0120000 A1 | 5/2017 | Osypka et al. | |
| 2017/0128700 A1 | 5/2017 | Roche Rebollo | |
| 2017/0143890 A1 | 5/2017 | Nardeo | |
| 2017/0172653 A1 | 6/2017 | Urbanski et al. | |
| 2017/0239443 A1 | 8/2017 | Abitabilo et al. | |
| 2017/0273628 A1 | 9/2017 | Ofek et al. | |
| 2017/0273713 A1 | 9/2017 | Shah et al. | |
| 2017/0296792 A1 | 10/2017 | Ornelas Vargas et al. | |
| 2017/0326339 A1 | 11/2017 | Bailey et al. | |
| 2017/0326349 A1 | 11/2017 | Pagano, II et al. | |
| 2017/0361070 A1 | 12/2017 | Hivert | |
| 2018/0021545 A1 | 1/2018 | Mitchell et al. | |
| 2018/0116690 A1 | 5/2018 | Sarabia et al. | |
| 2018/0117284 A1 | 5/2018 | Appling et al. | |
| 2018/0133438 A1 | 5/2018 | Hulvershorn et al. | |
| 2018/0154062 A1 | 6/2018 | DeFonzo et al. | |
| 2018/0154112 A1 | 6/2018 | Chan et al. | |
| 2018/0214674 A1 | 8/2018 | Ebnet et al. | |
| 2018/0296799 A1 | 10/2018 | Horst et al. | |
| 2018/0296804 A1 | 10/2018 | Bierman | |
| 2019/0015646 A1 | 1/2019 | Matlock et al. | |
| 2019/0060616 A1 | 2/2019 | Solomon | |
| 2019/0076167 A1 | 3/2019 | Fantuzzi et al. | |
| 2019/0134349 A1 | 5/2019 | Cohn et al. | |
| 2019/0201665 A1 | 7/2019 | Turpin | |
| 2019/0255294 A1 | 8/2019 | Mitchell et al. | |
| 2019/0276268 A1 | 9/2019 | Akingba | |
| 2019/0321590 A1 | 10/2019 | Burkholz et al. | |
| 2020/0016374 A1 | 1/2020 | Burkholz et al. | |
| 2020/0121211 A1 | 4/2020 | Tutino | |
| 2021/0069471 A1 | 3/2021 | Howell | |
| 2021/0121661 A1 | 4/2021 | Howell | |
| 2021/0121667 A1 | 4/2021 | Howell | |
| 2021/0128879 A1 | 5/2021 | Seidenberger | |
| 2021/0322729 A1 | 10/2021 | Howell | |
| 2021/0330941 A1 | 10/2021 | Howell et al. | |
| 2021/0330942 A1 | 10/2021 | Howell | |
| 2021/0361915 A1 | 11/2021 | Howell et al. | |
| 2021/0402142 A1 | 12/2021 | Howell et al. | |
| 2021/0402149 A1 | 12/2021 | Howell | |
| 2021/0402153 A1 | 12/2021 | Howell et al. | |
| 2022/0001138 A1 | 1/2022 | Howell | |
| 2022/0032013 A1 | 2/2022 | Howell et al. | |
| 2023/0256199 A1 | 8/2023 | Howell | |
| 2023/0256209 A1 | 8/2023 | Mckinnon et al. | |

(56) References Cited

U.S. PATENT DOCUMENTS

FOREIGN PATENT DOCUMENTS

| EP | 1458437 B1 | 3/2010 |
|----|------------|--------|
| EP | 2248549 A2 | 11/2010 |
| EP | 2319576 A1 | 5/2011 |
| EP | 2366422 A1 | 9/2011 |
| EP | 2486880 A2 | 8/2012 |
| EP | 2486881 A2 | 8/2012 |
| EP | 2486951 A2 | 8/2012 |
| EP | 2152348 B1 | 2/2015 |
| EP | 3093038 B1 | 5/2019 |
| EP | 2260897 B1 | 9/2019 |
| GB | 1273547 A | 5/1972 |
| WO | 94/21315 A1 | 9/1994 |
| WO | 95/32009 A2 | 11/1995 |
| WO | 98/44979 A1 | 10/1998 |
| WO | 98/53871 A1 | 12/1998 |
| WO | 99/12600 A1 | 3/1999 |
| WO | 99/26681 A1 | 6/1999 |
| WO | 2003008020 A1 | 1/2003 |
| WO | 2003057272 A2 | 7/2003 |
| WO | 2003066125 A2 | 8/2003 |
| WO | 2004050144 A2 | 6/2004 |
| WO | 2006055288 A2 | 5/2006 |
| WO | 2006055780 A2 | 5/2006 |
| WO | 2007046850 A2 | 4/2007 |
| WO | 2008033983 A1 | 3/2008 |
| WO | 2008092029 A2 | 7/2008 |
| WO | 2008/131300 A2 | 10/2008 |
| WO | 2008131289 A2 | 10/2008 |
| WO | 2009114833 A1 | 9/2009 |
| WO | 2009114837 A2 | 9/2009 |
| WO | 2010/048449 A2 | 4/2010 |
| WO | 2010056906 A2 | 5/2010 |
| WO | 2010083467 A2 | 7/2010 |
| WO | 2010/132608 A2 | 11/2010 |
| WO | 2011081859 A2 | 7/2011 |
| WO | 2011097639 A2 | 8/2011 |
| WO | 2011146764 A1 | 11/2011 |
| WO | 2012068162 A2 | 5/2012 |
| WO | 2012068166 A2 | 5/2012 |
| WO | 2012135761 A1 | 10/2012 |
| WO | 2012162677 A1 | 11/2012 |
| WO | 2013026045 A1 | 2/2013 |
| WO | 2013138519 A1 | 9/2013 |
| WO | 2014006403 A1 | 1/2014 |
| WO | 2014/100392 A1 | 6/2014 |
| WO | 2014113257 A2 | 7/2014 |
| WO | 2014152005 A2 | 9/2014 |
| WO | 2014197614 A2 | 12/2014 |
| WO | 2015057766 A1 | 4/2015 |
| WO | 2015/166157 A1 | 11/2015 |
| WO | 2016110824 A1 | 7/2016 |
| WO | 2016123278 A1 | 8/2016 |
| WO | 2016139590 A1 | 9/2016 |
| WO | 2016139597 A2 | 9/2016 |
| WO | 2016176065 A1 | 11/2016 |
| WO | 2017127074 A1 | 7/2017 |
| WO | 2018089275 A1 | 5/2018 |
| WO | 2018089285 A1 | 5/2018 |
| WO | 2018089385 A1 | 5/2018 |
| WO | 2018191547 A1 | 10/2018 |
| WO | 2018213148 A1 | 11/2018 |
| WO | 2018218236 A1 | 11/2018 |
| WO | 2019/034320 A1 | 2/2019 |
| WO | 2019/040801 A1 | 2/2019 |
| WO | 2019/146026 A1 | 8/2019 |
| WO | 2019199734 A1 | 10/2019 |
| WO | 2020069395 A1 | 4/2020 |
| WO | 2021050302 A1 | 3/2021 |
| WO | 2021/062023 A1 | 4/2021 |
| WO | 2021/077103 A1 | 4/2021 |
| WO | 2021081205 A1 | 4/2021 |
| WO | 2021086793 A1 | 5/2021 |
| WO | 2022133297 A1 | 6/2022 |
| WO | 2023/158613 A1 | 8/2023 |
| WO | 2023/158709 A1 | 8/2023 |

OTHER PUBLICATIONS

PCT/US2020/052536 filed Sep. 24, 2020 International Search Report and Written Opinion dated Dec. 4, 2020.

PCT/US2020/056364 filed Oct. 19, 2020 International Search Report and Written Opinion dated Jan. 19, 2021.

PCT/US2020/056864 filed Oct. 22, 2020 International Search Report and Written Opinion dated Jan. 14, 2021.

PCT/US2020/057202 filed Oct. 23, 2020 International Search Report and Written Opinion dated Jan. 21, 2021.

PCT/US2020/057397 filed Oct. 26, 2020 International Search Report and Written Opinion dated Mar. 10, 2021.

PCT/US2021/014700 filed Jan. 22, 2021 International Search Report and Written Opinion dated Jun. 29, 2021.

U.S. Appl. No. 16/398,020, filed Apr. 29, 2019 Non-Final Office Action dated May 11, 2021.

PCT/US2021/039843 filed Jun. 30, 2021 International Search Report and Written Opinion dated Nov. 11, 2021.

PCT/US2021/044029 filed Jul. 30, 2021 International Search Report and Written Opinion dated Dec. 9, 2021.

U.S. Appl. No. 16/398,020, filed Apr. 29, 2019 Final Office Action dated Jan. 25, 2022.

U.S. Appl. No. 15/008,628, filed Jan. 28, 2016 Final Office Action dated May 30, 2018.

U.S. Appl. No. 15/008,628, filed Jan. 28, 2016 Non-Final Office Action dated Jan. 25, 2019.

U.S. Appl. No. 15/008,628, filed Jan. 28, 2016 Non-Final Office Action dated Nov. 2, 2017.

U.S. Appl. No. 15/008,628, filed Jan. 28, 2016 Notice of Allowance dated May 15, 2019.

PCT/US2021/028018 filed Apr. 19, 2021 International Search Report and Written Opinion dated Sep. 13, 2021.

PCT/US2021/028683 filed Apr. 22, 2021 International Search Report and Written Opinion dated Sep. 16, 2021.

PCT/US2021/029183 filed Apr. 26, 2021 International Search Report and Written Opinion dated Sep. 24, 2021.

PCT/US2021/033443 filed May 20, 2021 International Search Report and Written Opinion dated Sep. 23, 2021.

PCT/US2020/056364 filed Oct. 19, 2020 International Preliminary Report on Patentability dated Apr. 19, 2022.

PCT/US2020/056864 filed Oct. 22, 2020 International Preliminary Report on Patentability dated Apr. 26, 2022.

PCT/US2021/036445 filed Jun. 8, 2021 International Search Report and Written Opinion dated Dec. 21, 2021.

PCT/US2021/039398 filed Jun. 28, 2021 International Search Report and Written Opinion dated Nov. 5, 2021.

U.S. Appl. No. 17/074,405, filed Oct. 19, 2020 Non-Final Office Action dated Mar. 31, 2023.

U.S. Appl. No. 17/074,405, filed Oct. 19, 2020 Restriction Requirement dated Jan. 17, 2023.

U.S. Appl. No. 17/080,578, filed Oct. 26, 2020 Non-Final Office Action dated Mar. 31, 2023.

U.S. Appl. No. 17/080,578, filed Oct. 26, 2020 Restriction Requirement dated Dec. 15, 2022.

U.S. Appl. No. 17/342,285, filed Jun. 8, 2021 Restriction Requirement dated May 2, 2023.

PCT/US2023/012931 filed Feb. 13, 2023 International Search Report and Written Opinion dated May 25, 2023.

PCT/US2023/013165 filed Feb. 15, 2023 International Search Report and Written Opinion dated Jun. 13, 2023.

U.S. Appl. No. 17/342,285, filed Jun. 8, 2021 Non-Final Office Action dated Aug. 1, 2023.

U.S. Appl. No. 17/360,746, filed Jun. 28, 2021 Non-Final Office Action dated Jun. 29, 2023.

U.S. Appl. No. 17/360,746, filed Jun. 28, 2021 Final Office Action dated Nov. 6, 2023.

U.S. Appl. No. 17/342,285, filed Jun. 8, 2021 Final Office Action dated Mar. 7, 2025.

(56) References Cited

OTHER PUBLICATIONS

U.S. Appl. No. 17/360,746, filed Jun. 28, 2021 Examiner's Answer dated Mar. 13, 2025.

EP 20878324.1 filed Mar. 11, 2022 Extended European Search Report dated Jan. 3, 2024.

U.S. Appl. No. 17/074,405, filed Oct. 19, 2020 Final Office Action dated Jan. 18, 2024.

U.S. Appl. No. 17/080,578, filed Oct. 26, 2020 Final Office Action dated Feb. 27, 2024.

U.S. Appl. No. 17/342,285, filed Jun. 8, 2021 Non-Final Office Action dated Dec. 22, 2023.

U.S. Appl. No. 17/342,285, filed Jun. 8, 2021 Non-Final Office Action dated Sep. 28, 2024.

U.S. Appl. No. 17/080,578, filed Oct. 26, 2020 Advisory Action dated Apr. 11, 2024.

U.S. Appl. No. 17/342,285, filed Jun. 8, 2021 Final Office Action dated Apr. 25, 2024.

U.S. Appl. No. 17/360,746, filed Jun. 28, 2021 Non-Final Office Action dated Mar. 19, 2024.

U.S. Appl. No. 17/080,578, filed Oct. 26, 2020 Non-Final Office Action dated Oct. 17, 2025.

U.S. Appl. No. 18/110,300, filed Feb. 15, 2023 Non-Final Office Action dated Nov. 26, 2025.

* cited by examiner

SECTION C or D 532
528
530
214,314

SECTION B 526
216

SECTION A 212
524

RAPIDLY INSERTABLE CENTRAL CATHETER AND METHODS THEREOF

CROSS-REFERENCE

This application claims the benefit of priority to U.S. Provisional Patent Application No. 62/924,582 filed Oct. 22, 2019, which is incorporated by reference in its entirety into this application.

BACKGROUND

A central venous catheter ("CVC") is formed of a material having a relatively low durometer, which contributes to the CVC having a lack of column strength. Due to the lack of column strength, CVCs are commonly introduced into patients and advanced through vasculatures thereof by way of the Seldinger technique. The Seldinger technique utilizes a number of steps and medical devices (e.g., a needle, a scalpel, a guidewire, an introducer sheath, a dilator, a CVC, etc.). While the Seldinger technique is effective, the number of steps are time consuming, handling the number of medical devices is awkward, and both of the foregoing can lead to patient trauma. In addition, there is a relatively high potential for touch contamination due to the number of medical devices that need to be interchanged during the number of steps of the Seldinger technique. As such, there is a need to reduce the number of steps and medical devices involved in introducing a catheter into a patient and advancing the catheter through a vasculature thereof.

Disclosed herein are rapidly insertable central catheters ("RICCs") and methods thereof that address the foregoing.

SUMMARY

Disclosed herein is a RICC including, in some embodiments, a catheter tube, a suture wing disposed over a medial portion of the catheter tube, a hub coupled to a proximal-end portion of the catheter tube, and a number of extension legs extending from the hub. The catheter tube includes a first section in a distal portion of the catheter tube formed of a first polymeric material having a first durometer. The catheter tube also includes a second section proximal of the first section of the catheter tube formed of a second polymeric material having a second durometer less than the first durometer. The catheter tube has a column strength sufficient to prevent buckling of the catheter tube when inserted into an insertion site and advanced through a vasculature of a patient. The number of extension legs extending from the hub is equal to a number of lumens extending through the RICC.

In some embodiments, the catheter tube between the suture wing and the hub is a single catheter tube configured to abate bacterial ingress between a dressing applied over the suture wing and skin of the patient. Being a single catheter tube enables the dressing to be pinched more tightly around the catheter tube than possible for multiple extension legs, which extend from suture wing-hub combinations common to existing central venous catheters or peripherally inserted central catheters.

In some embodiments, the catheter tube between the suture wing and the hub is configured to mitigate patient discomfort from proximity of the number of extension legs to a head or neck of the patient. The catheter tube is flexible enough to enable the catheter tube to be bent away from the head or neck of the patient and secured to the patient.

In some embodiments, the first section of the catheter tube is polytetrafluoroethylene, polypropylene, or polyurethane.

In some embodiments, the second section of the catheter tube is bump tubing. The suture wing is disposed over a bump in the second section of the catheter tube such that the catheter tube proximal of the suture wing has a larger outer diameter than the catheter tube distal of the suture wing.

In some embodiments, the catheter tube further includes a third section proximal of the second section of the catheter tube. The third section of the catheter tube has a larger outer diameter than the second section of the catheter tube. The suture wing is disposed over a proximal-end portion of the second section of the catheter tube and a distal-end portion of the third section of the catheter tube.

In some embodiments, the third section of the catheter tube is polyvinyl chloride, polyethylene, polyurethane, or silicone.

In some embodiments, the second section of the catheter tube is polyvinyl chloride, polyethylene, polyurethane, or silicone.

In some embodiments, the RICC is a triluminal catheter including a trifurcated hub having three extension legs extending from the trifurcated hub. Each extension leg of the three extension legs includes a Luer connector coupled to a proximal-end portion of the extension leg.

In some embodiments, the RICC includes a first lumen extending from an opening in a proximal end of a first Luer connector to an opening in a distal end of the first section of the catheter tube. The RICC also includes a second lumen extending from an opening in a proximal end of a second Luer connector to a first eyelet in the second section of the catheter tube. The RICC also includes a third lumen extending from an opening in a proximal end of a third Luer connector to a second eyelet in the second section of the catheter tube.

In some embodiments, the RICC is a diluminal catheter including a bifurcated hub having two extension legs extending from the bifurcated hub. Each extension leg of the two extension legs includes a Luer connector coupled to a proximal-end portion of the extension leg.

In some embodiments, the RICC includes a first lumen extending from an opening in a proximal end of a first Luer connector to an opening in a distal end of the first section of the catheter tube. The RICC also includes a second lumen extending from an opening in a proximal end of a second Luer connector to an eyelet in the second section of the catheter tube.

Also disclosed herein is a RICC including, in some embodiments, a catheter tube, a suture wing disposed over a medial portion of the catheter tube, a hub coupled to a proximal-end portion of the catheter tube, and three extension legs extending from the hub. The catheter tube includes a first section in a distal portion of the catheter tube formed of a first polymeric material having a first durometer. The catheter tube also includes a second section proximal of the first section of the catheter tube formed of bump tubing of a second polymeric material having a second durometer less than the first durometer. The catheter tube has a column strength sufficient to prevent buckling of the catheter tube when inserted into an insertion site and advanced through a vasculature of a patient without the Seldinger technique. The suture wing is disposed over a bump in the second section of the catheter tube such that the catheter tube proximal of the suture wing has a larger outer diameter than the catheter tube distal of the suture wing. Each extension leg of the three extension legs has a Luer connector coupled to a proximal-end portion of the extension leg.

In some embodiments, the RICC includes a first lumen extending from an opening in a proximal end of a first Luer connector to an opening in a distal end of the first section of the catheter tube. The RICC also includes a second lumen extending from an opening in a proximal end of a second Luer connector to a first eyelet in the second section of the catheter tube. The RICC also includes a third lumen extending from an opening in a proximal end of a third Luer connector to a second eyelet in the second section of the catheter tube.

In some embodiments, the catheter tube between the suture wing and the hub is configured to abate bacterial ingress between a dressing applied over the suture wing and skin of the patient. The catheter tube enables the dressing to be pinched more tightly around the catheter tube than possible for multiple extension legs, which extend from suture wing-hub combinations common to existing central venous catheters or peripherally inserted central catheters.

In some embodiments, the catheter tube between the suture wing and the hub is configured to mitigate patient discomfort from proximity of the number of extension legs to a head or neck of the patient. The catheter tube is flexible enough to enable the catheter tube to be bent away from the head or neck of the patient and secured to the patient.

Also disclosed herein is a method of a RICC including, in some embodiments, a creating step of creating an insertion site to access a vasculature of a patient with a needle disposed within a lumen of the RICC. The RICC includes a catheter tube having a first section in a distal portion of the catheter tube and a second section proximal of the first section of the catheter tube. The first section of the catheter tube is formed of a first polymeric material with a first durometer and the second section of the catheter tube is formed of a second polymeric material with a second durometer less than the first durometer. The method further includes an inserting step of inserting a distal-end portion of the catheter tube into the insertion site. The method further includes an advancing step of advancing the catheter tube through the vasculature of the patient. The advancing step further includes inserting the catheter tube farther into the insertion site without having to use a Seldinger technique. The Seldinger technique need not be used due to the catheter tube having a column strength sufficient to prevent buckling of the catheter tube when inserted into the insertion site and advanced through the vasculature of the patient.

In some embodiments, the method further includes a withdrawing step of withdrawing the needle from the lumen of the RICC after creating the insertion site and inserting at least some of the first section of the catheter tube into the insertion site.

In some embodiments, the insertion site is at a right subclavian vein or a right internal jugular vein.

In some embodiments, the advancing step further includes advancing the first section of the catheter tube through the right subclavian vein or the right internal jugular vein, a right brachiocephalic vein, and into a superior vena cava.

Also disclosed herein is a RICC including, in some embodiments, a catheter tube, a suture wing disposed over a medial portion of the catheter tube, a hub coupled to a proximal-end portion of the catheter tube, and a number of extension legs extending from the hub. The catheter tube includes a first section in a distal portion of the catheter tube formed of a first polymeric material. The catheter tube also includes a second section proximal of the first section of the catheter tube formed of a second polymeric material having a substantially equal durometer to the first polymeric material. The catheter tube has a column strength sufficient to prevent buckling of the catheter tube when inserted into an insertion site and advanced through a vasculature of a patient. The number of extension legs extending from the hub is equal to a number of lumens extending through the RICC.

These and other features of the concepts provided herein will become more apparent to those of skill in the art in view of the accompanying drawings and following description, which describe particular embodiments of such concepts in greater detail.

DRAWINGS

DESCRIPTION

Figure 1:
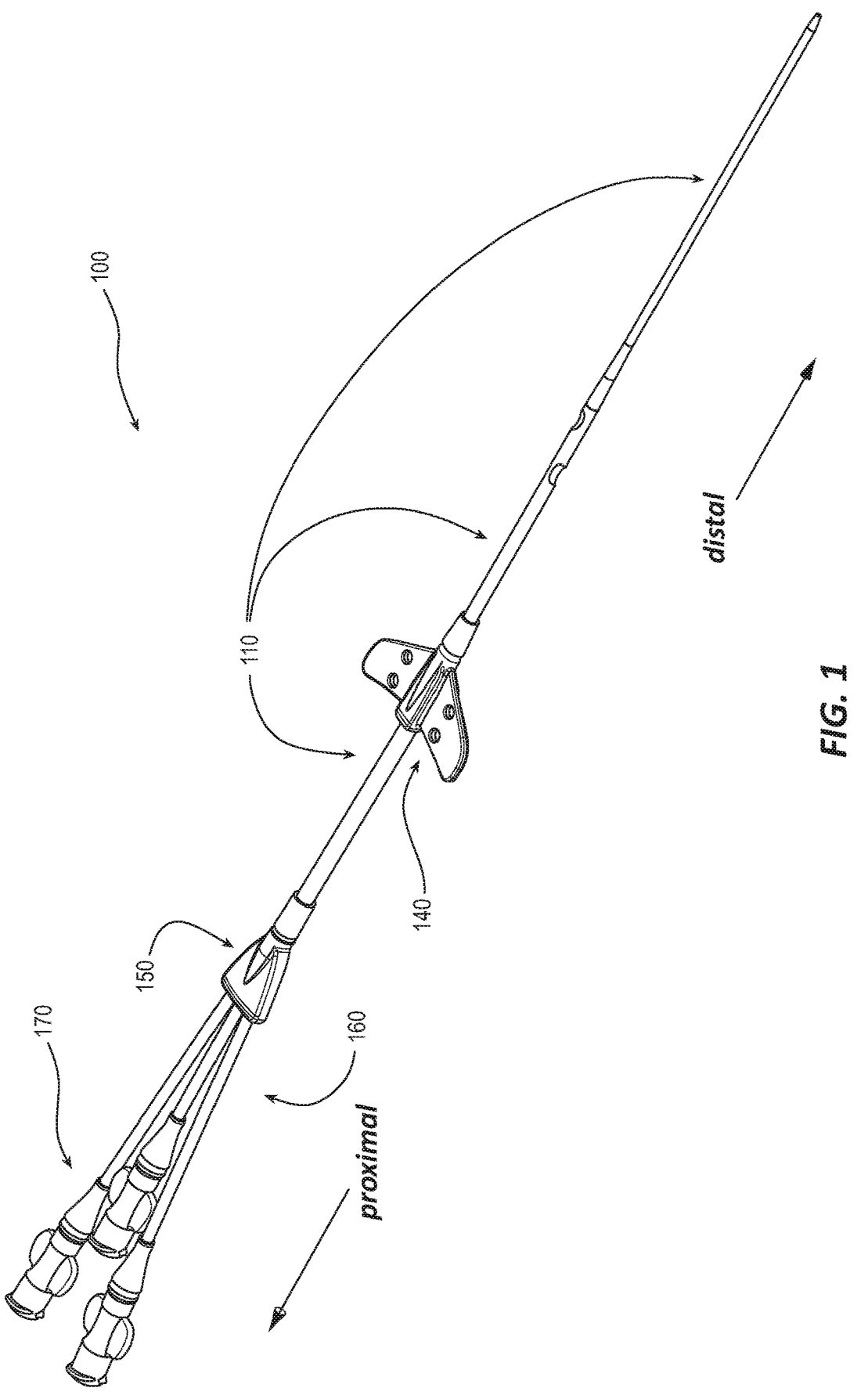
FIG. 1 illustrates an isometric view of a RICC in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, there is a need to reduce the number of steps and medical devices involved in introducing a catheter into a patient and advancing the catheter through a vasculature thereof. Disclosed herein are RICCs and methods thereof that address the foregoing.

Rapidly Insertable Central Catheters

FIG. 1 illustrates an isometric view of a RICC 100 in accordance with some embodiments.

As shown, the RICC 100 includes a catheter tube 110, a suture wing 140, a hub 150, and a number of extension legs 160 extending from the hub 150.

The suture wing 140 is disposed over a medial portion of the catheter tube 110 between a proximal-end portion and a distal-end portion of the catheter tube 110. Depending upon a chosen method of manufacturing, the suture wing 140 can be molded with a through hole longitudinally extending through the suture wing 140 configured for insertion of the catheter tube 110 (e.g., the second section 214 of the catheter tube 110 set forth below) therethrough. (See, for example, FIGS. 1 and 2.) Alternatively, the suture wing 140 can be molded over a number of core pins for a number of fluid pathways longitudinally extending through the suture wing 140 configured to fluidly connect a number of catheter-tube lumens of the catheter tube 110 distal of the suture wing 140 (e.g., the second section 314 of the catheter tube 110 set forth below) to a number of catheter-tube lumens of the catheter tube 110 proximal of the suture wing 140 (e.g., the third section 318 of the catheter tube 110 set forth below). (See, for example, FIGS. 1 and 3.) Alternatively, the suture wing 140 can be molded over a number of cannulas longitudinally extending through the suture wing 140 configured to fluidly connect the number of catheter-tube lumens of the catheter tube 110 distal of the suture wing 140 (e.g., the second section 314 of the catheter tube 110 set forth below) to the number of catheter-tube lumens of the catheter tube 110 proximal of the suture wing 140 (e.g., the third section 318 of the catheter tube 110 set forth below). (See, for example, FIGS. 1 and 3.)

The suture wing 140 includes a pair of wings 342 including a number of through holes 344 for suturing the suture wing 140 to a patient. (See FIG. 3.) Each wing of the pair of wings 342 can include one through hole, two through holes, three through holes, or four through holes for suturing the suture wing 140 to a patient.

The hub 150 is coupled to the proximal-end portion of the catheter tube 110 such as by insertion of the proximal-end portion of the catheter tube 110 into a bore in a distal-end portion of the hub 150. While not shown, the hub 150 also includes a number of bores in a proximal-end portion of the hub 150 corresponding in number to the number of extension legs 160. The number of bores in the distal-end portion of the hub 150 are configured to accept insertion of the number of extension legs 160 into the number of bores.

As set forth in more detail below, the RICC 100 can be a monoluminal catheter or a multiluminal catheter such as a diluminal catheter or a triluminal catheter. Accordingly, the hub 150 is either not furcated for the monoluminal catheter or furcated in accordance with a number of lumens extending through the RICC 100. For example, the hub 150 can be bifurcated for the diluminal catheter or trifurcated for the triluminal catheter. Depending upon a chosen method of manufacturing, the hub 150 can be molded over a number of core pins for a number of fluid pathways longitudinally extending through the hub 150 configured to fluidly connect the number of catheter-tube lumens of the catheter tube 110 to a number of extension-leg lumens of the number of extension legs 160. Alternatively, the hub 150 can be molded over a number of cannulas longitudinally extending through the hub 150 configured to fluidly connect the number of catheter-tube lumens of the catheter tube 110 to the number of extension-leg lumens of the number of extension legs 160.

The number of extension legs 160 extend from the hub 150 by way of their distal-end portions. The number of extension legs 160 is equal to the number of lumens extending through the RICC 100. For example: If the RICC 100 is a monoluminal catheter, one extension leg extends from the hub 150. If the RICC 100 is a diluminal catheter, two extension legs extend from the hub 150. If the RICC 100 is a triluminal catheter, three extension legs extend from the hub 150.

The RICC 100 further includes a number of Luer connectors 170 for fluidly connecting a number of medical devices to the RICC 100. Each extension leg of the number of extension legs 160 includes a Luer connector of the number of Luer connectors 170 coupled to a proximal-end portion of the extension leg. Given the foregoing, the number of Luer connectors 170 is equal to the number of extension legs 160, which number of extension legs 160, in turn, is equal to the number of lumens extending through the RICC 100. For example: If the RICC 100 is a monoluminal catheter, one extension leg extends from the hub 150 and one Luer connector is coupled to the extension leg. If the RICC 100 is a diluminal catheter, two extension legs extend from the hub 150 and two Luer connectors are respectively coupled to the two extension legs. If the RICC 100 is a triluminal catheter, three extension legs extend from the hub 150 and three Luer connectors are respectively coupled to the three extension legs.

Two genera of the catheter tube 110 are set forth below in two embodiments. Distinguishing features of a first embodiment of the catheter tube 110 are initially introduced and distinguishing features of a second embodiment of the catheter tube 110 are subsequently introduced. For expository expediency, various features of the two embodiments of the catheter tube 110 are described thereafter, some of which features are common between the two embodiments of the catheter tube 110, and some of which features are unique to the first embodiment or the second embodiment of the catheter tube 110. Other features of the RICC 100 are described after the catheter tube 110 and elsewhere herein.

Figure 2:
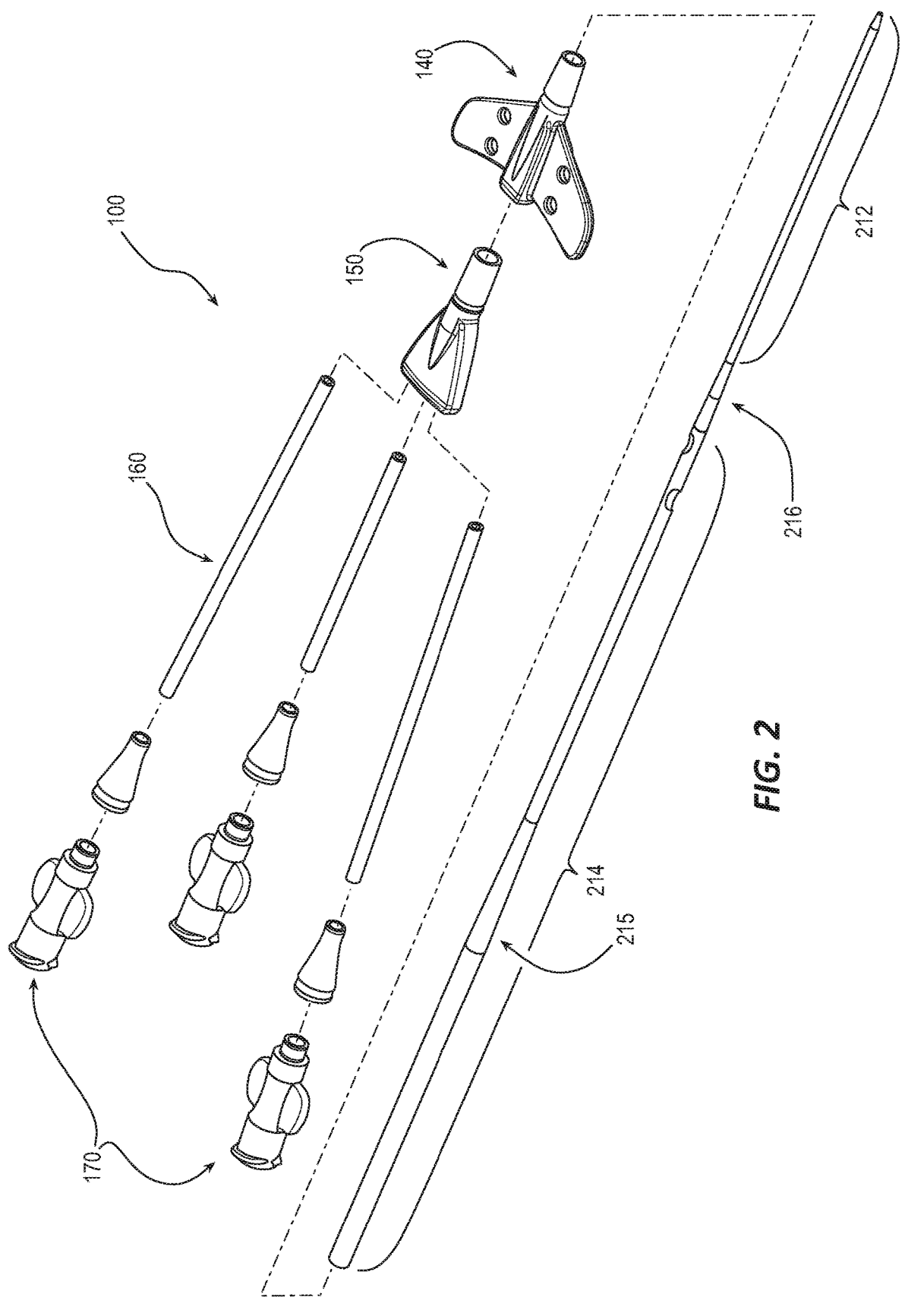
FIG. 2 illustrates an exploded view of the RICC in accordance with some embodiments.

FIG. 2 illustrates an exploded view of the RICC 100 in accordance with the first embodiment of the catheter tube 110.

As shown, the first embodiment of the catheter tube 110 includes a first section 212 and a second section 214 of the catheter tube 110 with an optional section 216 therebetween depending upon the manner in which the first section 212 and the second section 214 of the catheter tube 110 are coupled during manufacturing. The manner in which the first section 212 and the second section 214 of the catheter tube 110 are coupled is described in U.S. Provisional Application No. 62/905,363, filed Sep. 24, 2019, and in U.S. Provisional Application No. 62/898,408, filed Sep. 10, 2019, each of which is incorporated in its entirety into this application. (See also U.S. Provisional Application No. 62/923,320, filed Oct. 18, 2019, which is incorporated in its entirety into this application.) For example, any two sections of the first, second, and third sections coupled together as set forth herein can be coupled together by bonding (e.g., solvent bonding) or welding (e.g., RF welding). The third section or junction 140, 240, or 340 of the catheter tube 110, 210, or 310 in the aforementioned provisional applications corresponds to the optional section 216 between the first section 212 and the second section 214 of the first embodiment of the catheter tube 110.

Figure 3:
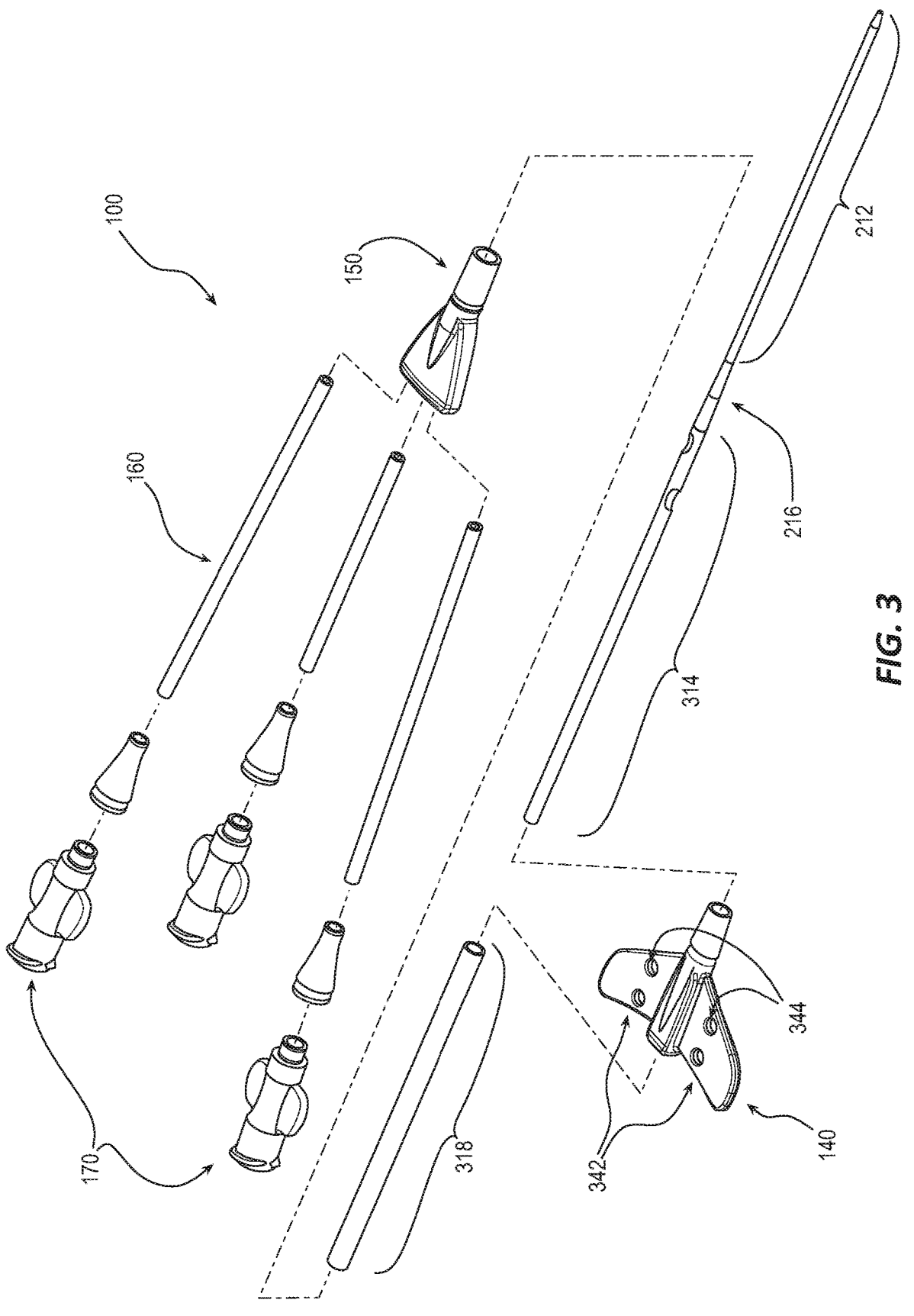
FIG. 3 illustrates an exploded view of the RICC in accordance with some embodiments.

FIG. 3 illustrates an exploded view of the RICC 100 in accordance with a second embodiment of the catheter tube 110.

As shown, the second embodiment of the catheter tube 110 includes the first section 212 and a second section 314 of the catheter tube 110 with a third section 318 proximal of the second section 314 of the catheter tube 110. The optional section 216 can be between the first section 212 and the second section 314 of the second embodiment of the catheter tube 110 depending upon the manner in which the first section 212 and the second section 314 of the catheter tube 110 are coupled during manufacturing. As with the first embodiment of the catheter tube 110, the manner in which the first section 212 and second section 314 of the second embodiment of the catheter tube 110 are coupled is described in the aforementioned provisional applications. The third section or junction 140, 240, or 340 of the catheter tube 110, 210, or 310 in the aforementioned provisional applications corresponds to the optional section 216 between the first section 212 and the second section 214 of the first embodiment of the catheter tube 110.

In view of the foregoing, the catheter tube 110 can include two sections up to at least four sections depending upon a chosen method of manufacturing the RICC 100. Among such embodiments of the catheter tube 110, two sections of the catheter tube 110 are common: the first section 212 in a distal portion of the catheter tube 110 and the second section 214 or 314 proximal of the first section of the catheter tube 110.

The first section 212 of the catheter tube 110 is formed of a first polymeric material (e.g., polytetrafluoroethylene, polypropylene, or polyurethane) having a first durometer, while the second section 214 or 314 is formed of a second polymeric material (e.g., polyvinyl chloride, polyethylene, polyurethane, or silicone) having a second durometer less than the first durometer. For example, each section of the first section 212 and the second section 214 or 314 of the catheter tube 110 can be made from a different polyurethane having a different durometer. Indeed, polyurethane is advantageous in that polyurethane sections of the catheter tube 110 can be relatively rigid at room-temperature but become more flexible in vivo at body temperature, which reduces irritation to vessel walls and phlebitis. Polyurethane is also advantageous in that can be less thrombogenic than some other polymers.

It should be understood the first durometer and the second durometer can be on different scales (e.g., Type A or Type D), so the second durometer of the second polymeric material might not be numerically less than the first durometer of the first polymeric material. That said, the hardness of the second polymeric material can still be less than the hardness of the first polymeric material as the different scales—each of which ranges from 0 to 100—are designed for characterizing different materials in groups of the materials having a like hardness.

Notwithstanding the foregoing, the first section 212 and the second section 214 or 314 of the catheter tube 110 can be formed of a same polymeric material or different polymeric materials having substantially equal durometers provided a column strength of the catheter tube 110 is sufficient to prevent buckling of the catheter tube 110 when inserted into an insertion site and advanced through a vasculature of a patient.

The catheter tube 110 having at least the first section 212 of the first polymeric material and the second section 214 or 314 of the second polymeric material has a column strength sufficient to prevent buckling of the catheter tube 110 when the catheter tube 110 is inserted into an insertion site and advanced through a vasculature of a patient. The column strength of the catheter tube 110 is notable in that it makes it possible to rapidly insert the catheter tube 110 into the insertion site and advance the catheter tube 110 through the vasculature of the patient without the using the Seldinger technique.

Adverting to the first embodiment of the catheter tube 110 shown in FIG. 2, the second section 214 of the catheter tube 110 includes a bumped diameter indicated by a bump 215 in a medial portion of the second section 214 of the catheter tube 110. A proximal portion of the second section 214 of the catheter tube 110 has a larger outer diameter than a distal portion of the second section 214 of the catheter tube 110. When the suture wing 140 is disposed over the bump 215 as shown in FIG. 1, the catheter tube 110 proximal of the suture wing 140—also known as a catheter-tube extension herein—has a larger outer diameter than the catheter tube 110 distal of the suture wing 140. The larger outer diameter of the second section 214 of the catheter tube 110 proximal of the suture wing 140 provides a thicker, more kink-resistant catheter-tube wall useful for bending the hub 150 and the number of extension legs 160 away from a head or neck of a patient while the RICC 100 is in use. In addition, any lumens present in the catheter tube 110 can have a greater diameter in the second section 214 of the catheter tube 110 proximal of the suture wing 140 than distal of the suture wing 140. This prevents flow rate reduction, particularly when the second section 214 of the catheter tube 110 proximal of the suture wing 140 is bent away from a head or neck of a patient. The second section 214 of the catheter tube 110 can be formed of a single extrusion of bump tubing.

Adverting to the second embodiment of the catheter tube 110 shown in FIG. 3, the second section 314 and the third section 318 of the catheter tube 110, together, simulate the bumped diameter of the second section 214 of the first embodiment of the catheter tube 110. The third section 318 of the catheter tube 110 has a larger outer diameter than the second section 214 of the catheter tube 110. When the suture wing 140 is disposed over a proximal-end portion of the second section 314 of the catheter tube 110 and a distal-end portion of the third section 318 of the catheter tube 110, the catheter tube 110 proximal of the suture wing 140 (i.e., the third section 318 of the catheter tube 110)—also known as the catheter-tube extension—has a larger outer diameter than the catheter tube 110 distal of the suture wing 140 (i.e., the second section 314 of the catheter tube 110). Like that set forth above with respect to the second section 214 of the catheter tube 110, the larger outer diameter of the third section 318 of the catheter tube 110 proximal of the suture wing 140 provides a thicker, more kink-resistant catheter-tube wall useful for bending the hub 150 and the number of extension legs 160 away from a head or neck of a patient while the RICC 100 is in use. In addition, any lumens present in the catheter tube 110 can have a greater diameter in the third section 318 of the catheter tube 110 than in the second section 314 of the catheter tube 110. This prevents flow rate reduction, particularly when the third section 318 of the catheter tube 110 proximal of the suture wing 140 is bent away from a head or neck of a patient. Like the second section 214 or 314 of the catheter tube 110, the third section 318 of the catheter tube 110 can be polyvinyl chloride, polyethylene, polyurethane, or silicone.

Whether of the first embodiment or the second embodiment of the catheter tube 110, the catheter tube 110 between the suture wing 140 and the hub 150 can have a reverse taper in which the larger outer diameter of the catheter tube 110 continues to increase from the suture wing 140 to the hub 150. In other words, the catheter tube 110 tapers from the hub 150 to the suture wing 140 but continues to have a larger outer diameter than the catheter tube 110 distal of the suture wing 140. In association with the continuously increasing outer diameter of the catheter tube 110 from the suture wing 140 to the hub 150, the catheter-tube wall can continuously increase in thickness, any lumens of the catheter tube 110 can continuously increase in cross-sectional area, or a combination thereof. Consequently, the catheter tube 110 between the suture wing 140 and the hub 150 can be more resistant to kinks and flow rate reduction, particularly when the catheter tube 110 proximal of the suture wing 140 is bent away from a head or neck of a patient.

The catheter tube 110 between the suture wing 140 and the hub 150, which section of the catheter tube 110 is also known as the catheter-tube extension herein, is a single catheter tube configured to abate bacterial ingress between a dressing applied over the suture wing 140 and skin of a patient. Existing CVCs or peripherally inserted central catheters ("PICCs") have multiple extension legs extending from suture wing-hub combinations common to the CVCs and PICCs. The multiple extension legs in the CVCs or PICCs provide multiple pathways under the dressing for microbial ingress. The catheter tube 110 being a single catheter tube enables the dressing to be pinched more tightly around the catheter tube 110 than possible for the multiple extension legs of the existing CVCs or PICCs. For example, the dressing can be easily wrapped around an entirety of the catheter tube 110 and pinched together under the catheter tube 110 or between the catheter tube 110 and the patient. In contrast, even wrapping the dressing around the multiple extension legs of the existing CVCs or PICCs leaves gaps between the extension tubes. Thus, the catheter tube 110 being a single catheter tube limits bacterial ingress between the dressing applied over the suture wing 140 and the skin of the patient.

The catheter tube 110 between the suture wing 140 and the hub 150, which section of the catheter tube 110 is also known as the catheter-tube extension herein, is also configured to mitigate patient discomfort from proximity of the number of extension legs 160 to a head or neck of the patient. As set forth above, the second section 214 or the third section 318 of the catheter tube 110 proximal of the suture wing 140 provides a thicker, more kink-resistant catheter-tube wall; however, the second section 214 or the third section 318 of the catheter tube 110 is flexible enough to enable the catheter tube 110 to be bent away from the head or neck of the patient and secured to the patient for his or her comfort.

Figure 4:
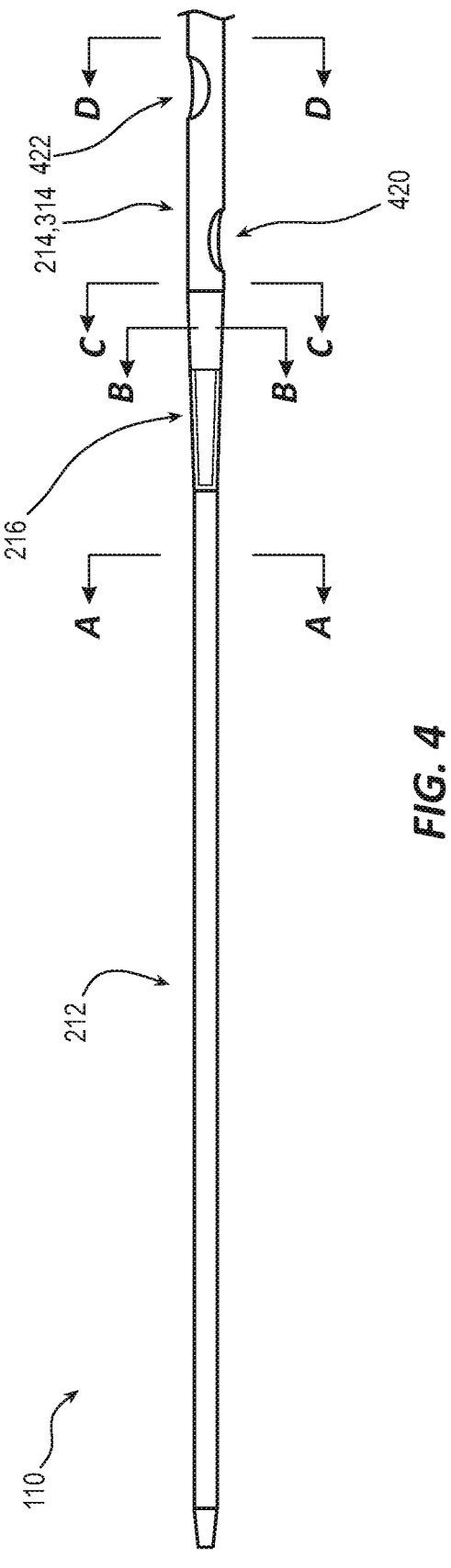
FIG. 4 illustrates a distal portion of a catheter tube of the RICC in accordance with some embodiments.
Figure 5C:
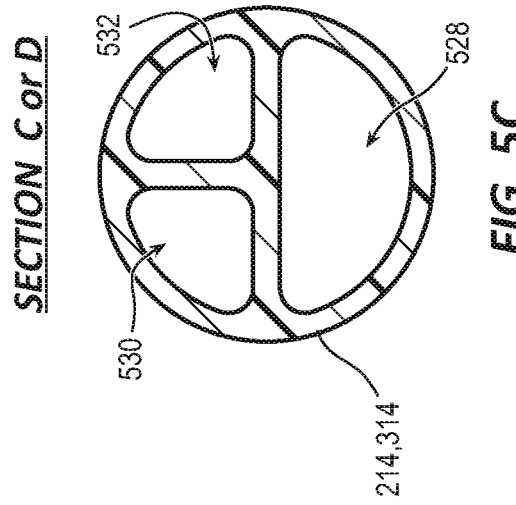
FIG. 5C illustrates a third transverse or fourth cross section of the catheter tube of the RICC in accordance with some embodiments.
Figure 5B:
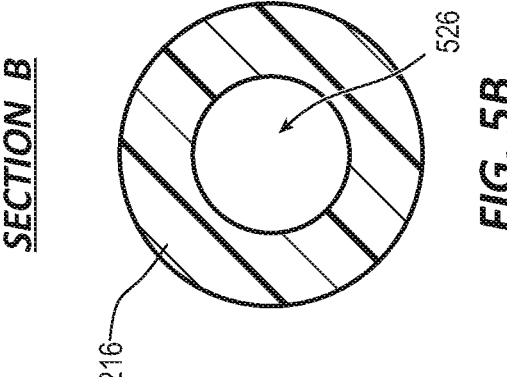
FIG. 5B illustrates a second transverse cross section of the catheter tube of the RICC in accordance with some embodiments.
Figure 5A:
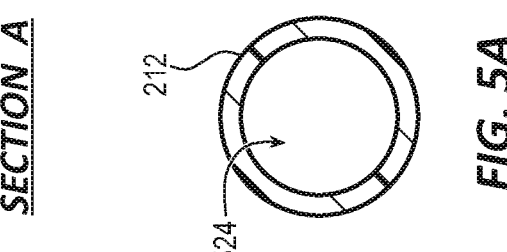
FIG. 5A illustrates a first transverse cross section of the catheter tube of the RICC in accordance with some embodiments.

FIG. 4 illustrates the distal portion of the catheter tube 110 of the RICC 100 in accordance with some embodiments. FIGS. 5A-5C illustrate different transverse cross sections of the catheter tube 110 of the RICC 100 in accordance with some embodiments.

The RICC 100 can be a monoluminal catheter or a multiluminal catheter such as a diluminal catheter, a triluminal catheter, a tetraluminal catheter, a pentaluminal catheter, or a hexaluminal catheter.

When the RICC 100 is configured as a triluminal catheter as shown in FIGS. 4 and 5A-5C, the RICC 100 includes a first lumen, a second lumen, and a third lumen. The first lumen extends from an opening in a tip or distal end of the first section 212 of the catheter tube 110 to an opening in a proximal end of a first Luer connector of the number of Luer connectors 170. The second lumen extends from an eyelet 420 in a distal-end portion of the second section 214 or 314 of the catheter tube 110 to an opening in a proximal end of a second Luer connector of the number of Luer connectors 170. The third lumen extends from an eyelet 422 in the distal-end portion of the second section 214 or 314 of the catheter tube 110 proximal of the eyelet 420 to an opening in a proximal end of a third Luer connector of the number of Luer connectors 170. Each lumen of the first lumen, the second lumen, and the third lumen is further described in a separate paragraph set forth below.

The first lumen of the RICC 100 includes fluidly connected luminal sections including a lumen 524 of the first section 212 of the catheter tube 110, a lumen 526 of the optional section 216 of the catheter tube 110, when the optional section 216 is present, and a first lumen 528 of the second section 214 or 314 of the catheter tube 110. If the catheter tube 110 is that of the second embodiment of the catheter tube 110, the fluidly connected luminal sections of the first lumen of the RICC 100 further include a first fluid passageway or first cannula lumen of the suture wing 140 and a first lumen of the third section 318 of the catheter tube 110. (The first lumen of the third section 318 of the catheter tube 110 is not shown as it is akin to the first lumen 528 of the second section 314 of the catheter tube 110.) Whether the catheter tube 110 is that of the second or third embodiment of the catheter tube 110, the fluidly connected luminal sections of the first lumen of the RICC 100 further include a first fluid passageway or first cannula lumen of the hub 150, a first extension-leg lumen of a first extension leg (e.g., the extension leg labeled "distal" in FIGS. 1-3) of the number of extension legs 160, and a first Luer-connector lumen of the first Luer connector of the number of Luer connectors 170.

The second lumen of the RICC 100 includes fluidly connected luminal sections including a second lumen 530 of the second section 214 or 314 of the catheter tube 110, which extends from the eyelet 420 in the distal-end portion of the second section 214 or 314 of the catheter tube 110. If the catheter tube 110 is that of the second embodiment of the catheter tube 110, the fluidly connected luminal sections of the second lumen of the RICC 100 further include a second fluid passageway or second cannula lumen of the suture wing 140 and a second lumen of the third section 318 of the catheter tube 110. (The second lumen of the third section 318 of the catheter tube 110 is not shown as it is akin to the second lumen 530 of the second section 314 of the catheter tube 110.) Whether the catheter tube 110 is that of the second or third embodiment of the catheter tube 110, the fluidly connected luminal sections of the second lumen of the RICC 100 further include a second fluid passageway or second cannula lumen of the hub 150, a second extension-leg lumen of a second extension leg (e.g., the extension leg labeled "medial" in FIGS. 1-3) of the number of extension legs 160, and a second Luer-connector lumen of the second Luer connector of the number of Luer connectors 170.

The third lumen of the RICC 100 includes fluidly connected luminal sections including a third lumen 532 of the second section 214 or 314 of the catheter tube 110, which extends from the eyelet 422 in the distal-end portion of the second section 214 or 314 of the catheter tube 110. If the catheter tube 110 is that of the second embodiment of the catheter tube 110, the fluidly connected luminal sections of the third lumen of the RICC 100 further include a third fluid passageway or third cannula lumen of the suture wing 140 and a third lumen of the third section 318 of the catheter tube 110. (The third lumen of the third section 318 of the catheter tube 110 is not shown as it is akin to the third lumen 532 of the second section 314 of the catheter tube 110.) Whether the catheter tube 110 is that of the second or third embodiment of the catheter tube 110, the fluidly connected luminal sections of the third lumen of the RICC 100 further include a third fluid passageway or third cannula lumen of the hub 150, a third extension-leg lumen of a third extension leg (e.g., the extension leg labeled "proximal" in FIGS. 1-3) of the number of extension legs 160, and a third Luer-connector lumen of the third Luer connector of the number of Luer connectors 170.

When the RICC 100 is configured as a diluminal catheter, the RICC 100 includes a first lumen and a second lumen. Like the RICC 100 when configured as the triluminal catheter, the first lumen extends from an opening in a tip or distal end of the first section 212 of the catheter tube 110 to an opening in a proximal end of a first Luer connector of the number of Luer connectors 170. The second lumen extends from an eyelet akin to the eyelet 420 in the distal-end portion of the second section 214 or 314 of the catheter tube 110 to an opening in a proximal end of a second Luer connector of the number of Luer connectors 170. Because the first lumen and the second lumen of the RICC 100 configured as the diluminal catheter are analogous to the first lumen and the second lumen of the RICC 100 configured as the triluminal catheter, additional detail for each lumen of the first lumen and the second lumen of the RICC 100 configured as the diluminal catheter can be discerned from the description set forth above for the first lumen and the second lumen of the RICC 100 configured as the triluminal catheter.

When the RICC 100 is configured as a monoluminal catheter, the RICC 100 includes a single lumen, which single lumen is also known as a first lumen herein for consistency with description set forth above. Like the RICC 100 when configured as the triluminal catheter, the first lumen extends from an opening in a tip or distal end of the first section 212 of the catheter tube 110 to an opening in a proximal end of a first Luer connector of the number of Luer connectors 170. Because the first lumen of the RICC 100 configured as the monoluminal catheter is analogous to the first lumen of the RICC 100 configured as the triluminal catheter, additional detail for the first lumen of the RICC 100 configured as the monoluminal catheter can be discerned from the description set forth above for the first lumen of the RICC 100 configured as the triluminal catheter.

Methods

A method for making the RICC 100 includes one or more extruding steps of extruding one or more extrudable components, one or more molding steps of molding one or more moldable components, and one or more assembling steps of assembling the RICC 100 or any portion thereof by coupling the extrudable and moldable components together.

The one or more extruding steps can include extruding any one or more sections of the catheter tube 110 selected from the first section 212 of the catheter tube 110, the second section 214 or 314 of the catheter tube 110, the optional section 216 of the catheter tube 110, and the third section 318 of the catheter tube 110 in accordance with description set forth above for the foregoing one or more sections of the catheter tube 110. The one or more extruding steps can further include extruding any one or more extension legs of the number of extension legs 160 in accordance with description set forth above for the one or more extension legs.

The one or more molding steps includes molding any one or more moldable components selected from the suture wing 140 and the hub 150 in accordance with description set forth above for the one or more moldable components. The one or more molding steps can further include molding any one or more Luer connectors of the number of Luer connectors 170 in accordance with description set forth above for the one or more Luer connectors.

The one or more assembling steps of assembling the RICC 100 or any portion thereof can include coupling the first section 212 of the catheter tube 110 to the second section 214 or 314 of the catheter tube 110 either directly or indirectly through the optional section 216 of the catheter tube 110 as described in U.S. Provisional Patent Application Nos. 62/923,320 and 62/898,408 filed, Oct. 18, 2019, and Sep. 6, 2019, respectively, each of which is incorporated herein in its entirety. The foregoing incorporation by reference includes any other steps desired in support of coupling the first section 212 of the catheter tube 110 to the second section 214 or 314 of the catheter tube 110.

A method of using the RICC 100 includes a creating step of creating an insertion site to access a vasculature of a patient with a needle disposed within a lumen of the RICC 100. The insertion site can be at a subclavian vein such as a right or left subclavian vein, an internal jugular vein such as a right or left internal jugular vein, or a femoral vein.

The method further includes an inserting step of inserting the distal-end portion of the catheter tube 110 into the insertion site.

The method further includes a withdrawing step of withdrawing the needle from the lumen of the RICC 100 after creating the insertion site and inserting at least some of the first section 212 of the catheter tube 110 into the insertion site.

The method further includes an advancing step of advancing the catheter tube 110 through the vasculature of the patient without having to use the Seldinger technique. For example, if the insertion site is at the right subclavian vein or the right internal jugular vein, the advancing step can further include inserting the catheter tube 110 farther into the insertion site such that the catheter tube 110 or at least the distal-end portion thereof is advanced through the right subclavian vein or the right internal jugular vein, a right brachiocephalic vein, and into a superior vena cava. Other insertions sites such as at the left subclavian vein or the left internal jugular vein require advancing the distal-end portion of the catheter tube 110 through corresponding vasculature. The Seldinger technique need not be used due to the catheter tube 110 having a column strength sufficient to prevent buckling of the catheter tube 110 when inserted into the insertion site and advanced through the vasculature of the patient.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A rapidly insertable central catheter ("RICC"), comprising:
a catheter tube including:
a first section in a distal portion of the catheter tube formed of a first polymeric material having a first durometer; and
a second section proximal of the first section of the catheter tube formed of a second polymeric material having a second durometer less than the first durometer, the catheter tube having a column strength sufficient to prevent buckling of the catheter tube when inserted into an insertion site and advanced through a vasculature of a patient, wherein the second section of the catheter tube is bump tubing;
a suture wing disposed over a medial portion of the catheter tube, the suture wing disposed over a bump in the second section of the catheter tube such that the catheter tube proximal of the suture wing has a larger outer diameter than the catheter tube distal of the suture wing;
a hub coupled to a proximal-end portion of the catheter tube;
a number of extension legs extending from the hub equal to a number of lumens extending through the RICC;
a first lumen extending from a proximal end of the RICC to a distal end of the RICC; and
a second lumen extending from the proximal end of the RICC to a distal end of the second section, the second lumen terminating at the first section of the catheter tube or a junction between the first and second sections of the catheter tube.

2. The RICC of claim 1, wherein the catheter tube between the suture wing and the hub is a single catheter tube configured to abate bacterial ingress between a dressing applied over the suture wing and skin of the patient by enabling the dressing to be pinched more tightly around the single catheter tube than possible for multiple extension legs extending from suture wing-hub combinations common to existing central venous catheters or peripherally inserted central catheters.

3. The RICC of claim 1, wherein the catheter tube between the suture wing and the hub is configured to mitigate patient discomfort from proximity of the number of extension legs to a head or neck of the patient by being flexible enough to enable the catheter tube to be bent away from the head or neck of the patient and secured to the patient.

4. The RICC of claim 1, wherein the first section of the catheter tube is polytetrafluoroethylene, polypropylene, or polyurethane.

5. The RICC of claim 1, wherein the catheter tube further includes a third section proximal of the second section of the catheter tube having a larger outer diameter than the second section of the catheter tube, the suture wing disposed over a proximal-end portion of the second section of the catheter tube and a distal-end portion of the third section of the catheter tube.

6. The RICC of claim 5, wherein the third section of the catheter tube is polyvinyl chloride, polyethylene, polyurethane, or silicone.

7. The RICC of claim 1, wherein the second section of the catheter tube is polyvinyl chloride, polyethylene, polyurethane, or silicone.

8. The RICC of claim 1, wherein the RICC is a triluminal catheter including a trifurcated hub for the hub and three extension legs for the number of extension legs, each extension leg of the three extension legs including a proximal-end portion having a Luer connector coupled thereto.

9. The RICC of claim 8, wherein the RICC further includes a third lumen, the first lumen extending from an opening in a proximal end of a first Luer connector of a first extension leg of the three extension legs to an opening in a distal end of the first section of the catheter tube, the second lumen extending from an opening in a proximal end of a second Luer connector of a second extension leg of the three extension legs to a first eyelet in a distal portion of the second section of the catheter tube, and the third lumen extending from an opening in a proximal end of a third Luer connector of a third extension leg of the three extension legs to a second eyelet in the distal portion of the second section of the catheter tube.

10. The RICC of claim 1, wherein the RICC is a diluminal catheter including a bifurcated hub for the hub and two extension legs for the number of extension legs, each extension leg of the two extension legs including a proximal-end portion having a Luer connector coupled thereto.

11. The RICC of claim 10, wherein the first lumen extends from an opening in a proximal end of a first Luer connector of a first extension leg of the two extension legs to an opening in a distal end of the first section of the catheter tube and the second lumen extends from an opening in a proximal end of a second Luer connector of a second extension leg of the two extension legs to an eyelet in a distal portion of the second section of the catheter tube.

12. A rapidly insertable central catheter ("RICC"), comprising:
a catheter tube including:
a first section in a distal portion of the catheter tube formed of a first polymeric material having a first durometer; and
a second section proximal of the first section of the catheter tube formed of bump tubing of a second polymeric material having a second durometer less than the first durometer, the catheter tube having a column strength sufficient to prevent buckling of the catheter tube when inserted into an insertion site and advanced through a vasculature of a patient without use of a Seldinger technique;

a suture wing disposed over a medial portion of the catheter tube, the suture wing disposed over a bump in the second section of the catheter tube such that the catheter tube proximal of the suture wing has a larger outer diameter than the catheter tube distal of the suture wing;

a hub coupled to a proximal-end portion of the catheter tube; and three extension legs extending from the hub, each extension leg of the three extension legs including a proximal-end portion having a Luer connector coupled thereto;

a first lumen extending from a proximal end of the RICC to a distal end of the RICC;

a second lumen extending from the proximal end of the RICC to a distal portion of the second section; and a third lumen extending from the proximal end of the RICC to the distal portion of the second section, the second and third lumens terminating at the first section of the catheter tube or a junction between the first and second sections of the catheter tube.

13. The RICC of claim 12, wherein the first lumen extends from an opening in a proximal end of a first Luer connector of a first extension leg of the three extension legs to an opening in a distal end of the first section of the catheter tube, the second lumen extends from an opening in a proximal end of a second Luer connector of a second extension leg of the three extension legs to a first eyelet in a distal portion of the second section of the catheter tube, and the third lumen extends from an opening in a proximal end of a third Luer connector of a third extension leg of the three extension legs to a second eyelet in the distal portion of the second section of the catheter tube.

14. The RICC of claim 12, wherein the catheter tube between the suture wing and the hub is configured to abate bacterial ingress between a dressing applied over the suture wing and skin of the patient by enabling the dressing to be pinched more tightly around the catheter tube than possible for multiple extension legs extending from suture wing-hub combinations common to existing central venous catheters or peripherally inserted central catheters.

15. The RICC of claim 12, wherein the catheter tube between the suture wing and the hub is configured to mitigate patient discomfort from proximity of the number of extension legs to a head or neck of the patient by being flexible enough to enable the catheter tube to be bent away from the head or neck of the patient and secured to the patient.

16. A rapidly insertable central catheter ("RICC"), comprising:

a catheter tube including:

a first section in a distal portion of the catheter tube formed of a first polymeric material; and a second section proximal of the first section of the catheter tube formed of a second polymeric material having a substantially equal durometer to the first polymeric material, the catheter tube having a column strength sufficient to prevent buckling of the catheter tube when inserted into an insertion site and advanced through a vasculature of a patient, wherein the second section of the catheter tube is bump tubing;

a suture wing disposed over a medial portion of the catheter tube, the suture wing disposed over a bump in the second section of the catheter tube such that the catheter tube proximal of the suture wing has a larger outer diameter than the catheter tube distal of the suture wing;

a hub coupled to a proximal-end portion of the catheter tube; and a number of extension legs extending from the hub equal to a number of lumens extending through the RICC;

a first lumen extending from a proximal end of the RICC to a distal end of the RICC; and a second lumen extending from the proximal end of the RICC to a distal end of the second section, the second lumen terminating at the first section of the catheter tube or a junction between the first and second sections of the catheter tube.

*    *    *    *    *